(12) United States Patent
Worthen

(10) Patent No.: US 10,053,059 B1
(45) Date of Patent: Aug. 21, 2018

(54) DETECTION AND IDENTIFICATION OF OPAQUENESS OF VEHICLE WINDOWS

(71) Applicant: Ford Global Technologies, LLC, Dearborn, MI (US)

(72) Inventor: Reid William Kaufman Worthen, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 15/725,085

(22) Filed: Oct. 4, 2017

(51) Int. Cl.
| | |
|---|---|
| *G01N 21/55* | (2014.01) |
| *B60S 1/08* | (2006.01) |
| *B60H 1/00* | (2006.01) |
| *B60S 1/48* | (2006.01) |
| *G01N 21/88* | (2006.01) |
| *G01N 21/958* | (2006.01) |
| *G01N 21/15* | (2006.01) |
| *G01N 21/94* | (2006.01) |

(52) U.S. Cl.
CPC ........ *B60S 1/0822* (2013.01); *B60H 1/00785* (2013.01); *B60S 1/485* (2013.01); *G01N 2021/157* (2013.01); *G01N 2021/8841* (2013.01); *G01N 2021/945* (2013.01); *G01N 2021/9586* (2013.01)

(58) Field of Classification Search
CPC ........... G01N 21/958; G01N 2033/873; G01N 2021/9586; G01N 2021/435; G01N 27/223; B60S 1/0833; B60S 1/0862; B60R 2011/0026
USPC ......... 356/239.1, 239.4, 239.5, 237.1–237.5, 356/445; 318/643, 483, 70; 250/574, 250/223 B; 340/602
See application file for complete search history.

(56) References Cited

U.S. PATENT DOCUMENTS

| | | | |
|---|---|---|---|
| 4,439,021 A | 3/1984 | Gross | |
| 4,871,917 A | 10/1989 | O'Farrell | |
| 4,970,122 A | 11/1990 | Palaisamy | |
| 5,821,501 A | 10/1998 | Zorn | |
| 5,898,183 A * | 4/1999 | Teder | ................... B60S 1/0822 250/574 |
| 6,262,407 B1 | 7/2001 | Teder | |

(Continued)

FOREIGN PATENT DOCUMENTS

| | | |
|---|---|---|
| DE | 3328652 A1 | 2/1985 |
| DE | 102004047215 A1 | 4/2006 |

(Continued)

OTHER PUBLICATIONS

Windshield Wiper Problems; Jan. 30, 2017; AGCO Automotive Corporation, https://www.agcauto.com/.

*Primary Examiner* — Hoa Pham
(74) *Attorney, Agent, or Firm* — James P. Muraff; Neal, Gerber & Eisenberg LLP

(57) ABSTRACT

Method and apparatus are disclosed for detection and identification of opaqueness of vehicle windows. An example vehicle includes a window including an interior surface and an exterior surface, a light transmitter to emit light, and light sensors to measure the light. The light sensors include a first sensor offset from and a second sensor aligned with the interior surface. The light sensors also include a third sensor offset from and a fourth sensor aligned with the exterior surface. The example vehicle also includes a controller for detecting a source of opaqueness of the window via the light sensors.

20 Claims, 5 Drawing Sheets

(56) References Cited

U.S. PATENT DOCUMENTS

| | | | |
|---|---|---|---|
| 6,307,198 B1 | 10/2001 | Asakura | |
| 6,555,804 B1 | 4/2003 | Blasing | |
| 6,674,370 B2 | 1/2004 | Rodewald et al. | |
| 6,853,897 B2 | 2/2005 | Stam et al. | |
| 6,888,465 B2 | 5/2005 | Schmitt et al. | |
| 7,006,129 B1 | 2/2006 | McClure | |
| 7,184,074 B1 | 2/2007 | Jansen | |
| 7,253,898 B2 * | 8/2007 | Saikalis | B60S 1/0822 250/201.1 |
| 7,385,216 B2 * | 6/2008 | Yoshigoe | B60S 1/0822 250/227.25 |
| 7,420,671 B2 | 9/2008 | Sonda | |
| 7,847,255 B2 * | 12/2010 | Teder | B60S 1/0822 250/341.8 |
| 8,334,972 B2 * | 12/2012 | Thien | G01N 21/94 340/425.5 |
| 9,120,464 B2 | 9/2015 | Pack et al. | |
| 2002/0040964 A1 | 4/2002 | Dausmann | |
| 2005/0040151 A1 | 2/2005 | Drydek | |
| 2005/0174561 A1 | 8/2005 | Murakami | |
| 2006/0016097 A1 | 1/2006 | Chiang | |
| 2006/0016795 A1 | 1/2006 | Witzke | |
| 2009/0161109 A1 | 6/2009 | Wolf | |
| 2009/0315723 A1 | 12/2009 | Linsenmaier | |
| 2011/0168687 A1 | 7/2011 | Door | |
| 2016/0119586 A1 | 4/2016 | Riad et al. | |
| 2017/0115235 A1 | 4/2017 | Ohlsson et al. | |
| 2018/0022320 A1 | 1/2018 | Lee | |

FOREIGN PATENT DOCUMENTS

| | | |
|---|---|---|
| DE | 102005027087 A1 | 12/2006 |
| JP | 2008185531 A | 8/2008 |
| KR | 20080061620 A | 7/2008 |
| WO | WO 2014130049 A1 | 8/2014 |
| WO | WO 2015162322 A1 | 10/2015 |

* cited by examiner

US 10,053,059 B1

DETECTION AND IDENTIFICATION OF OPAQUENESS OF VEHICLE WINDOWS

CROSS-REFERENCE TO RELATED APPLICATIONS

This application is related to U.S. application Ser. No. 15/469,239 that was filed on Mar. 24, 2017, U.S. application Ser. No. 15/469,256 that was filed on Mar. 24, 2017, and U.S. application Ser. No. 15/469,270 that was filed on Mar. 24, 2017, which are incorporated herein by reference in their entireties.

TECHNICAL FIELD

The present disclosure generally relates to vehicle windows and, more specifically, to detection and identification of opaqueness of vehicle windows.

BACKGROUND

Generally, a vehicle includes a windshield, a rear window, and side windows that partially define a cabin of the vehicle and enable a driver and/or other occupant(s) (e.g., passengers) to view an area surrounding the vehicle. Oftentimes, the windshield is formed from laminated safety glass, and the side and rear windows are formed from tempered glass, laminated glass, polycarbonate, acrylic resins, and/or other materials.

SUMMARY

The appended claims define this application. The present disclosure summarizes aspects of the embodiments and should not be used to limit the claims. Other implementations are contemplated in accordance with the techniques described herein, as will be apparent to one having ordinary skill in the art upon examination of the following drawings and detailed description, and these implementations are intended to be within the scope of this application.

Example embodiments are shown for detection and identification of opaqueness of vehicle windows. An example disclosed vehicle includes a window including an interior surface and an exterior surface, a light transmitter to emit light, and light sensors to measure the light. The light sensors include a first sensor offset from and a second sensor aligned with the interior surface. The light sensors also include a third sensor offset from and a fourth sensor aligned with the exterior surface. The example disclosed vehicle also includes a controller for detecting a source of opaqueness of the window via the light sensors.

An example disclosed method includes emitting light via a light transmitter, collecting measurements of the light via light sensors. The light sensors include a first sensor offset from and a second sensor aligned with an interior surface of a vehicle window. The light sensors also include a third sensor offset from and a fourth sensor aligned with an exterior surface of the vehicle window. The example disclosed method also includes detecting, via a processor, a source of opaqueness of the vehicle window based upon a comparison of the measurements.

BRIEF DESCRIPTION OF THE DRAWINGS

For a better understanding of the invention, reference may be made to embodiments shown in the following drawings. The components in the drawings are not necessarily to scale and related elements may be omitted, or in some instances proportions may have been exaggerated, so as to emphasize and clearly illustrate the novel features described herein. In addition, system components can be variously arranged, as known in the art. Further, in the drawings, like reference numerals designate corresponding parts throughout the several views.

DETAILED DESCRIPTION OF EXAMPLE EMBODIMENTS

Figure 1:
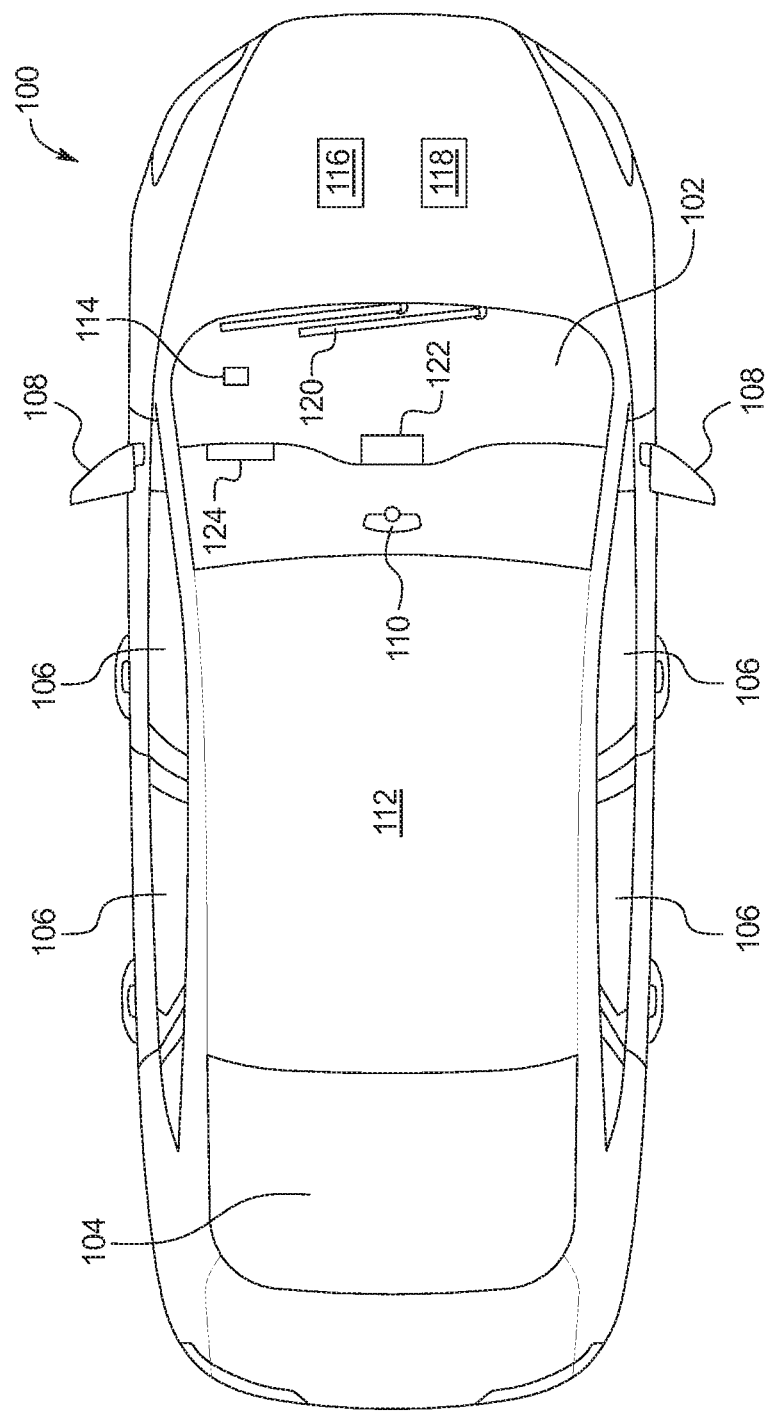
FIG. 1 illustrates an example vehicle in accordance with the teachings herein.

While the invention may be embodied in various forms, there are shown in the drawings, and will hereinafter be described, some exemplary and non-limiting embodiments, with the understanding that the present disclosure is to be considered an exemplification of the invention and is not intended to limit the invention to the specific embodiments illustrated.

Generally, a vehicle includes a windshield, a rear window, and side windows that partially define a cabin of the vehicle and enable a driver and/or other occupant(s) (e.g., passengers) to view an area surrounding the vehicle. Oftentimes, the windshield is formed from laminated safety glass, and the side and rear windows are formed from tempered glass, laminated glass, polycarbonate, acrylic resins, and/or other materials.

In some instances, a vehicle window becomes opaque due to material (e.g., rain, snow, ice, dirt, etc.) collecting on an exterior surface of the vehicle window, condensation forming on an interior surface of vehicle window, and/or imperfections (e.g., cracks, bubbles, etc.) formed within the vehicle window. For example, a film of condensation and/or ice forms on an interior surface of window(s) of the vehicle when a glass temperature is at or below a dew point temperature as a result of condensation collecting on a surface of the window(s). In some instances, condensation collects on an interior surface of a window when a temperature of the window is at or below a dew point temperature of air adjacent to the window. Additionally or alternatively, condensation that collects on an interior surface of a window may originate, at least in part, from moisture expelled by a vehicle occupant breathing, wet clothing, water and/or snow brought into the vehicle, etc. When vehicle window(s) are opaque (e.g., due to material collecting on an exterior surface, condensation forming on an interior surface, and/or imperfections formed within), it potentially may be become difficult for an operator (e.g., a driver) of the vehicle to view a surrounding area of the vehicle.

Example methods and apparatus disclosed herein include an opaqueness identification system of a vehicle that detects when opaque material has formed on and/or within a window the vehicle and identifies a source of the opaque material to facilitate a driver of the vehicle in removing the opaque material from the window of the vehicle.

Examples disclosed herein include a system for detecting opaqueness of a window of a vehicle. The system identifies whether a source of the opaqueness is located on an inner surface, on an outer surface, and/or within the window. The system includes light sensors at various locations relative to the window and a light source directed toward the light sensors. The system detects that the source of the opaqueness is on the inner surface (e.g., frost) if there is a difference in measured light between a first light sensor offset from the inner surface and a second light sensor on the inner surface. The system detects that the source of the opaqueness is on the outer surface (e.g., rain, snow, ice, dirt, etc.) if there is a difference in measured light between a third light sensor offset from the outer surface and a fourth light sensor on the outer surface. The system detects that the source of the opaqueness is within the window (e.g., a crack, a bubble, and/or other imperfection) if there is a difference in measured light between the second light sensor and the fourth light sensor and/or between the fourth light sensor and a fifth light sensor. The fifth light sensor is on the inner surface and measures light that reflects off the outer surface of the window.

Turning to the figures, FIG. 1 illustrates an example vehicle 100 in accordance with the teachings herein. The vehicle 100 may be a standard gasoline powered vehicle, a hybrid vehicle, an electric vehicle, a fuel cell vehicle, and/or any other mobility implement type of vehicle. The vehicle 100 includes parts related to mobility, such as a powertrain with an engine, a transmission, a suspension, a driveshaft, and/or wheels, etc. The vehicle 100 may be non-autonomous, semi-autonomous (e.g., some routine motive functions controlled by the vehicle 100), or autonomous (e.g., motive functions are controlled by the vehicle 100 without direct driver input).

In the illustrated example, the vehicle 100 includes a plurality of windows including a front windshield 102, a rear windshield 104 and side windows 106. For example, the front windshield 102 is formed of laminated and/or safety glass, and the rear windshield 104 and the side windows 106 are formed from non-laminated, tempered glass. In other examples, the front windshield 102, the rear windshield 104, and/or one or more of the side windows 106 are formed of any other material (e.g., polycarbonate, acrylic resins, etc.) that enables occupant(s) to view surrounding area(s) of the vehicle 100.

As illustrated in FIG. 1, the vehicle 100 also includes one or more side mirrors 108 (also referred to as wing mirrors, fender mirrors, etc.) and a rearview mirror 110. For example, the side mirrors 108 include a driver-side side mirror that enables an operator (e.g., a driver) to view an area next to and/or behind a driver side of the vehicle 100 and a passenger-side side mirror that enables the operator to view an area next to and/or behind a passenger side of the vehicle 100. In the illustrated example, each of the side mirrors 108 is coupled to and/or located next to a respective door of the vehicle 100 such that the operator views the surrounding areas via each of the side mirrors 108 through a corresponding one of the side windows 106. The rearview mirror 110 enables the operator to view an area behind the vehicle 100, for example, through the rear windshield 104. In the illustrated example is coupled to the front windshield 102 within a cabin 112 of the vehicle 100 to enable the operator to view the area behind the vehicle 100.

The vehicle 100 also includes an opaqueness detection assembly 114 that detects a presence and a source of opaqueness on one or more of the windows of the vehicle 100. In the illustrated example, the opaqueness detection assembly 114 is located on the front windshield 102 to monitor for opaqueness on the front windshield 102. Additionally or alternatively, the vehicle 100 includes an opaqueness detection assembly 114 that is located on the rear windshield 104 to monitor for opaqueness on the rear windshield 104 and/or an opaqueness detection assembly 114 that is located on one or more of the side windows 106 to monitor for opaqueness on the one or more of the side windows 106. As disclosed in further detail below, the opaqueness detection assembly 114 includes a light transmitter (e.g., a light transmitter 202 of FIG. 2) and a plurality of photo- or light sensors (e.g., a light sensor 214, a light sensor 216, a light sensor 218, a light sensor 220, and a light sensor 222 of FIG. 2) that enable an opaqueness controller 116 to detect whether the source of opaqueness is located on a an interior surface (e.g., an interior surface 210 of FIG. 2) of, located on a an exterior surface (e.g., an exterior surface 212 of FIG. 2) of, and/or embedded within a window of the vehicle 100.

The opaqueness controller 116 of the illustrated example is communicatively coupled (e.g., wired and/or wirelessly) to the light transmitter of the opaqueness detection assembly 114 to control characteristics of light (e.g., an intensity) that is transmitted by the light transmitter in a direction toward the sensors. Further, the opaqueness controller 116 is communicatively coupled (e.g., wired and/or wirelessly) to the sensors of the opaqueness detection assembly 114 to obtain measurements of the emitted light (e.g., light intensity measurements) that are collected by the sensors. The opaqueness controller 116 detects a presence and a source of the opaqueness upon comparing the measurements collected by each of the sensors. That is, the opaqueness controller 116 detects, based upon the light measurements collected by the opaqueness detection assembly 114, whether there are source(s) of opaqueness located along an interior surface (e.g., an interior surface 210 of FIG. 2), an exterior surface (e.g., an exterior surface 212 of FIG. 2), and/or embedded within a layer (e.g., a layer 208 of FIG. 2) of the front windshield 102, the rear windshield 104, and/or one or more of the side windows 106.

In some examples, the opaqueness controller 116 activates an HVAC system 118 in response to detecting that the source of opaqueness includes condensation (e.g., frost) on the interior surface of the front windshield 102, the rear windshield 104, and/or one or more of the side windows 106. For example, the HVAC system 118 is activated to remove the detected condensation from the interior surface by adjusting and/or otherwise affecting an environment within the cabin 112 of the vehicle 100. The HVAC system 118 of the illustrated example includes vents, a heater, and/or an air conditioner to control a temperature and/or a moisture level within the cabin 112 of the vehicle 100.

In some examples, the opaqueness controller 116 activates windshield wipers 120 in response to detecting that the source of opaqueness includes condensation (e.g., rain, snow, ice, etc.) and/or other opaque material (e.g., dirt, dust, mud, etc.) on the exterior surface of the front windshield 102. For example, the windshield wipers 120 are activated to remove the detected source of opaqueness from the exterior surface of the front windshield 102. Additionally or alternatively, the vehicle includes one or more windshield wipers 120 on the rear windshield 104 that the opaqueness controller 116 activates in response to detecting a source of opaqueness on the exterior surface of the front windshield 102. Further, the opaqueness controller 116 may activate a washer fluid system of the vehicle 100 to further facilitate removal of the source of opaqueness from the exterior surface of the front windshield 102 and/or the rear windshield 104.

As illustrated in FIG. 1, the vehicle 100 also includes a display 122 that presents an visual alert and/or one or more speakers 124 that present an audio alert in response to the opaqueness controller 116 detecting a source of opaqueness on the front windshield 102, the rear windshield 104, and/or one or more of the side windows 106. The alert(s) indicate to the operator that the opaqueness controller 116 has detected opaque material on a vehicle window, identify on which vehicle window(s) opaque material is located, and/or identify location(s) of the opaque material relative to the vehicle window(s). For example, the opaqueness controller 116 sends a signal to the display 122 and/or the speakers 124 to emit an alert identifying that a source of opaqueness has been detected along an interior surface, an exterior surface, and/or embedded within a layer of the front windshield 102, the rear windshield 104, and/or one or more of the side windows 106.

Figure 2:
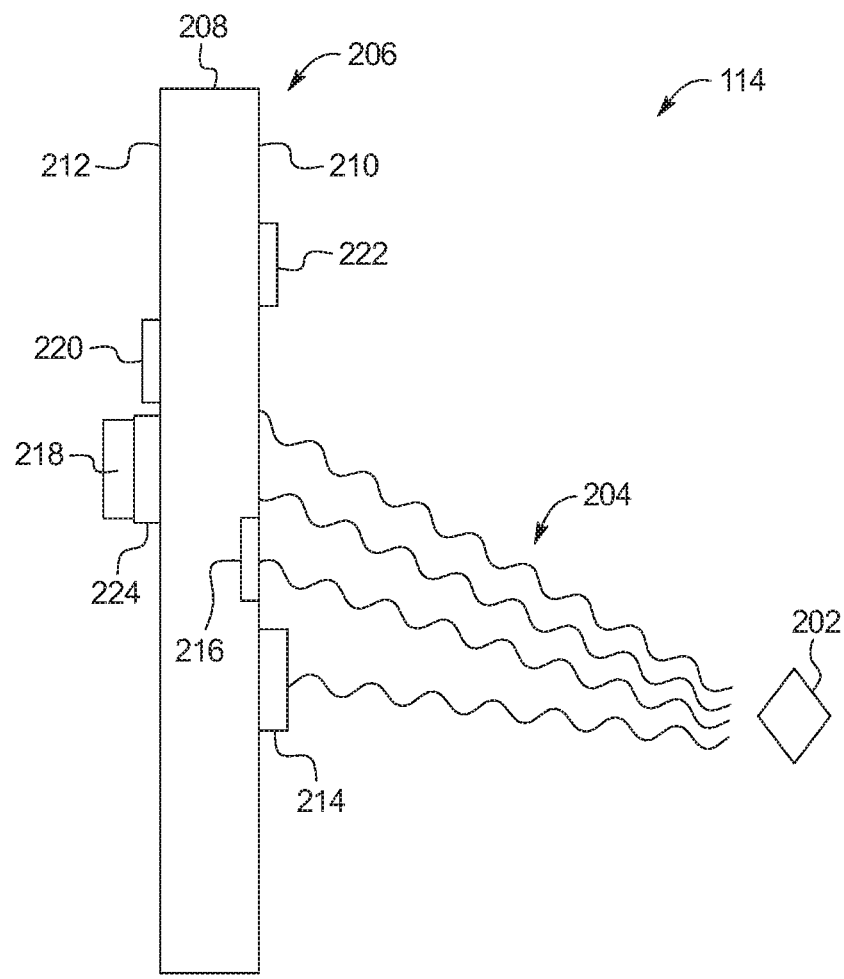
FIG. 2 depicts a cross-section of an opaqueness identification system and a window of the vehicle of FIG. 1.

FIG. 2 depicts a cross-section of the opaqueness detection assembly 114 of the vehicle 100. As illustrated in FIG. 2, the opaqueness detection assembly 114 includes a light transmitter 202 that emits light 204 toward a window 206 (e.g., the front windshield 102, the rear windshield 104, one of the side windows 106 of FIG. 1) of the vehicle 100. In the illustrated example, the window 206 is formed of a layer 208 of material (e.g., laminated glass, non-laminated glass, safety glass, tempered glass, polycarbonate, acrylic resins, etc.) that defines an inner or interior surface 210 and an outer or exterior surface 212 of the window 206. That is, the window 206 includes the layer 208, the interior surface 210, and the exterior surface 212. Further, in the illustrated example, the light 204 emitted by the light transmitter 202 is an unfocused light beam that directs light across an area of the window 206 to enable the opaqueness controller 116 to detect a source of opaqueness across that area of the window 206. In some examples, the light transmitter 202 is an LED transmitter and the light 204 that is unfocused is a scatter beam. In other examples, the light transmitter 202 is a laser transmitter and the light 204 that is unfocused is a Gaussian beam.

As illustrated in FIG. 2, the opaqueness detection assembly 114 also includes a plurality of light sensors including a light sensor 214 (also referred to as a first sensor, a first light sensor, a first photo-sensor), a light sensor 216 (also referred to as a second sensor, a second light sensor, a second photo-sensor), a light sensor 218 (also referred to as a third sensor, a third light sensor, a third photo-sensor), a light sensor 220 (also referred to as a fourth sensor, a fourth light sensor, a fourth photo-sensor), and a light sensor 222 (also referred to as a fifth sensor, a fifth light sensor, a fifth photo-sensor). The light sensors 214, 216, 218, 220, 222 collect measurements of the light 204 emitted by the light transmitter 202. For example, each of the light sensors 214, 216, 218, 220, 222 is an LED receiver, an infrared receiver, and/or any other photo- or light sensors that is configured to measure an intensity of the light 204 emitted by the light transmitter 202. Further, the light sensors 214, 216, 218, 220, 222 are spaced apart and/or offset from each in a such a manner that none of the light sensors 214, 216, 218, 220, 222 obstruct any other of the light sensors 214, 216, 218, 220, 222 from collecting the light 204 emitted by the light transmitter 202.

In the illustrated example, the light sensor 214 is coupled to the interior surface 210 of the window 206, for example, via an adhesive and/or a mechanical fastener. Further, a face of the light sensor 214 that collects the light 204 is facing toward the light transmitter 202. That is, as illustrated in FIG. 2, the face of the light sensor 214 that collects the light 204 is offset and facing away from the interior surface 210 of the window 206.

The light sensor 216 of the illustrated example is embedded within the layer 208 of the window 206 in such a manner that a face of the light sensor 216 that collects the light 204 is flush and/or substantially flush with the interior surface 210 of the window 206. That is, the face of the light sensor 216 that collects the light 204 is aligned with the interior surface 210 of the window 206 and facing the light transmitter 202.

Further, the light sensor 218 of the illustrated example is coupled to the exterior surface 212 of the window 206 via a bracket 224. For example, the light sensor 218 is coupled to the bracket 224 and the bracket 224 is coupled to the exterior surface 212 via an adhesive and/or a mechanical fastener. As illustrated in FIG. 2, a face of the light sensor 218 that collects the light 204 is facing toward the light transmitter 202 and the window 206. The bracket 224 to which the light sensor 218 is coupled enables the face of the light sensor 218 to be spaced apart and/or offset from the exterior surface 212 of the window 206.

As illustrated in FIG. 2, the light sensor 220 is coupled to the exterior surface 212 of the window 206, for example, via an adhesive and/or a mechanical fastener. Further, a face of the light sensor 220 that collects the light 204 is facing toward the light transmitter 202. That is, the face of the light sensor 220 that collects the light 204 engages and/or is even with the exterior surface 212 of the window 206.

Further, the light sensor 222 is coupled to the interior surface 210 of the window 206, for example, via an adhesive and/or a mechanical fastener. A face of the light sensor 222 that collects the light 204 engages and/or is even with the exterior surface 212 of the window 206. That is, the face of the light sensor 222 that collects the light 204 is facing toward the window 206 and away from the light transmitter 202 in a direction opposite to the face of the light sensor 214.

That is, in the illustrated example, the light transmitter 202 is located within the cabin 112 of the vehicle 100, the light sensors 214, 216, 222 are located along the interior surface 210 of the window 206, and the light sensors 218, 220 are location along the exterior surface 212 of the window 206. In other examples, the light transmitter 202 is located outside of the vehicle 100 next to the window 206, the light sensors 214, 216, 222 are located along the exterior surface 212 of the window 206, and the light sensors 218, 220 are location along the interior surface 210 of the window 206.

The measurements of light collected by the light sensors 214, 216, 218, 220, 222 of the illustrated example are utilized by the opaqueness controller 116 to detect a presence and a source of opaqueness on the window 206. For example, the opaqueness controller 116 determines whether there is a source of opaqueness on the interior surface 210 (e.g., frost), a source of opaqueness on the exterior surface 212 (e.g., rain, snow, ice, dirt, etc.), and/or a source of opaqueness within the layer 208 (e.g., (e.g., a crack, a bubble, and/or other imperfection) of the window 206 by comparing the light measurements collected by the light sensors 214, 216, 218, 220, 222. As disclosed in further detail below with respect to FIG. 3A, the opaqueness controller 116 determines whether opaque material is located on the interior surface 210 by comparing a first measurement of the light 204 collected by the light sensor 214 and a second measurement of the light 204 collected by the light sensor 216. As disclosed in further detail below with respect to FIG. 3B, the opaqueness controller 116 determines whether opaque material is located on the exterior surface 212 by comparing a third measurement of the light 204 collected by the light sensor 218 and a fourth measurement of the light 204 collected by the light sensor 220. As disclosed in further detail below with respect to FIG. 3C, the opaqueness controller 116 determines whether an opaque imperfection is formed within the layer 208 of the window 206 by comparing the fourth measurement of the light 204 collected by the light sensor 220 to the second measurement of the light 204 collected by the light sensor 216 and/or a fifth measurement of the light 204 collected by the light sensor 222.

FIG. 3A depicts the opaqueness detection assembly 114 detecting opaque material 302 that is a source of opaqueness on the interior surface 210 of the window 206. As illustrated in FIG. 3A, the light sensor 214 collects a first measurement of the light 204 emitted by the light transmitter 202, and the light sensor 216 collects a second measurement of the light 204 emitted by the light transmitter 202. For example, the light measurements correspond to a light intensity of the light 204 collected by the light sensors 214, 216. In such examples, the first measurement is a first light intensity of the light 204 as collected by the light sensor 214, and the second measurement is a second light intensity of the light 204 as collected by the light sensor 216.

Further, as illustrated in FIG. 3A, the light sensors 214, 216 are positioned relative to the window 206 and the light transmitter 202 such that the light 204 collected by both the light sensors 214, 216 are unaffected by the window 206. That is, because the light 204 collected by the light sensors 214, 216 do not travel into the layer 208 of the window 206, the intensity of the light 204 measured by the light sensor 214 and the intensity of the light 204 measured by the light sensor 216 are unaffected (e.g., not reduced) by the material that forms the window 206. As a result, the first measurement of the light sensor 214 is to equal the second measurement of the light sensor 216 when the opaque material 302 and/or any other source of opaqueness is not located on the interior surface 210 of the window 206. In contrast, when the opaque material 302 and/or any other source of opaqueness is located on the interior surface 210, the opaque material 302 affects (e.g., reduces) the intensity of the light 204 that is collected by the light sensor 216 and does not affect the intensity of the light 204 that is collected by the light sensor 214. In turn, the first measurement of the light sensor 214 is to be different than (e.g., greater than) the second measurement of the light sensor 216 when the opaque material 302 and/or any other source of opaqueness is located on the interior surface 210 of the window 206.

The affect that the opaque material 302 has on the light 204 collected by the light sensor 216 enables the opaqueness controller 116 to detect the presence of the opaque material 302 on the interior surface 210 of the window 206. That is, the opaqueness controller 116 detects whether there is a source of opaqueness (e.g., the opaque material 302) on the interior surface 210 of the window 206 by comparing the first measurement of the light sensor 214 and the second measurement of the light sensor 216. For example, the opaqueness controller 116 detects that a source of opaqueness (e.g., the opaque material 302) is located on the interior surface 210 in response to determining that the first measurement of the light sensor 214 is greater than the second measurement of the light sensor 216. In some examples, the opaqueness controller 116 detects that the opaque material 302 is condensation on the interior surface 210 in response to determining that the first measurement of the light sensor 214 is greater than the second measurement of the light sensor 216 by at least a first predetermined value. Further, in some examples, the opaqueness controller 116 identifies that frost is on the interior surface 210 of the window 206 in response to detecting that opaque material 302 on the interior surface 210 is condensation. Upon the opaqueness controller 116 detecting that frost and/or other condensation is on the interior surface 210 of the window 206, the opaqueness controller 116 is configured to activate and/or adjust the HVAC system 118 to remove the frost and/or other condensation from the window 206.

FIG. 3B depicts the opaqueness detection assembly 114 detecting the opaque material 302 that is a source of opaqueness on the exterior surface 212 of the window 206. As illustrated in FIG. 3B, the light sensor 218 collects a third measurement of the light 204 emitted by the light transmitter 202, and the light sensor 220 collects a fourth measurement of the light 204 emitted by the light transmitter 202. For example, the light measurements correspond to a light intensity of the light 204 collected by the light sensors 218, 220. In such examples, the third measurement is a third light intensity of the light 204 as collected by the light sensor 218, and the fourth measurement is a fourth light intensity of the light 204 as collected by the light sensor 220.

As illustrated in FIG. 3B, the light sensors 218, 220 are positioned relative to the window 206 and the light transmitter 202 such that the light 204 collected by both the light sensors 218, 220 are affected by the window 206. That is, because the light 204 collected by the light sensors 218, 220 travel through the width of the layer 208 of the window 206, the material forming the window 206 equally affects (e.g., reduces) the intensity of the light 204 measured by the light sensor 218 and the intensity of the light 204 measured by the light sensor 220. As a result, the third measurement of the light sensor 218 is to equal the fourth measurement of the light sensor 220 when the opaque material 302 and/or any other source of opaqueness is not located on the exterior surface 212 of the window 206. In contrast, when the opaque material 302 and/or any other source of opaqueness is located on the exterior surface 212, the opaque material 302 affects (e.g., reduces) the intensity of the light 204 that is collected by the light sensor 218 and does not affect the intensity of the light 204 that is collected by the light sensor 220. In turn, the third measurement of the light sensor 218 is different than (e.g., less than) the fourth measurement of the light sensor 220 when the opaque material 302 and/or any other source of opaqueness is located on the exterior surface 212 of the window 206.

The affect that the opaque material 302 has on the light 204 collected by the light sensor 218 enables the opaqueness controller 116 to detect the presence of the opaque material 302 on the exterior surface 212 of the window 206. That is, the opaqueness controller 116 detects whether there is a source of opaqueness (e.g., the opaque material 302) on the exterior surface 212 of the window 206 by comparing the third measurement of the light sensor 218 and the second measurement of the light sensor 220. For example, the opaqueness controller 116 detects that a source of opaqueness (e.g., the opaque material 302) is located on the exterior surface 212 in response to determining that the third measurement of the light sensor 218 is less than the fourth measurement of the light sensor 220. In some examples, the opaqueness controller 116 detects that the opaque material 302 is condensation on the exterior surface 212 in response to determining that the third measurement of the light sensor 218 is less than the fourth measurement of the light sensor 220 by at least a second predetermined value. Further, in some examples, the opaqueness controller 116 identifies that the opaque material 302 on the exterior surface 212 of the window 206 is rain, snow, ice, dirt, and/or other material(s) based upon a difference between the third measurement of the light sensor 218 and the fourth measurement of the light sensor 220. For example, rain corresponds to a first difference, snow corresponds to a second difference, ice corresponds to a third difference, dirt corresponds to a fourth difference, etc. Further, the opaqueness controller 116 is configured to activate and/or adjust a setting of the windshield wipers 120 to remove the condensation from the window 206 upon detecting that the condensation is on the exterior surface 212 of the window 206.

FIG. 3C depicts the opaqueness detection assembly 114 detecting an imperfection 304 formed within the layer 208 that is a source of opaqueness of the window 206. In the illustrated example, the light sensor 216 collects the second measurement of the light 204 emitted by the light transmitter 202, the light sensor 220 collects the fourth measurement of the light 204 emitted by the light transmitter 202, and the light sensor 222 collects a fifth measurement of the light 204 emitted by the light transmitter 202. For example, the light measurements correspond to a light intensity of the light 204 collected by the light sensors 216, 220, 222. In such examples, the second measurement is the second light intensity of the light 204 as collected by the light sensor 216, the fourth measurement is the fourth light intensity of the light 204 as collected by the light sensor 220, and the fifth measurement is a fifth light intensity of the light 204 as collected by the light sensor 222.

As illustrated in FIG. 3C, the light sensor 220 is positioned relative to the window 206 and the light transmitter 202 such that the light 204 collected by the light sensor 220 is affected by the window 206. Further, the light sensor 216 is positioned relative to the window 206 and the light transmitter 202 such that the light 204 collected by the light sensor 216 is unaffected by the window 206. As a result, the fourth measurement of the light sensor 220 is to be less than the second measurement of the light sensor 216 by a predetermined amount when the layer 208 of the window 206 does not include an imperfection (e.g., the imperfection 304). In contrast, when the imperfection 304 is located within the layer 208 of the window 206, the imperfection 304 further affects (e.g., further reduces) the intensity of the light 204 collected by the light sensor 220 such that the fourth measurement is less than the second measurement by at least a third predetermined value. The affect that the imperfection 304 has on the light 204 collected by the light sensor 220 enables the opaqueness controller 116 to detect the presence of the imperfection 304 within the window 206. For example, the opaqueness controller 116 detects that the imperfection 304 is within the window 206 in response to determining that the fourth measurement of the light sensor 220 is less than the second measurement of the light sensor 216 by at least the third predetermined value. That is, the opaqueness controller 116 identifies that the imperfection 304 is located within the window 206 in response to detecting that a source of opaqueness is within the window 206.

Additionally or alternatively, the opaqueness controller 116 detects the presence of the imperfection 304 within the window 206 via the light sensor 220 and the light sensor 222. As illustrated in FIG. 3C, the light sensors 220, 222 are positioned relative to the window 206 and the light transmitter 202 such that the light 204 collected by both of the light sensors 220, 222 is affected by the window 206. As a result, the fourth measurement of the light sensor 220 is to be less than the fifth measurement of the light sensor 222 by at least a fourth predetermined value when the imperfection 304 is located within the layer 208 of the window 206. For example, the opaqueness controller 116 detects that the imperfection 304 is within the window 206 in response to determining that the fourth measurement is less than the fifth measurement by at least the fourth predetermined value. In contrast, because the fourth measurement is not to be less than the fifth measurement by at least the fourth predetermined value when a source of opaqueness (e.g., the imperfection 304) is located within the layer 208 of the window 206, the opaqueness controller 116 is able to detect when a source of imperfection is not located within the window 206.

Figure 3:
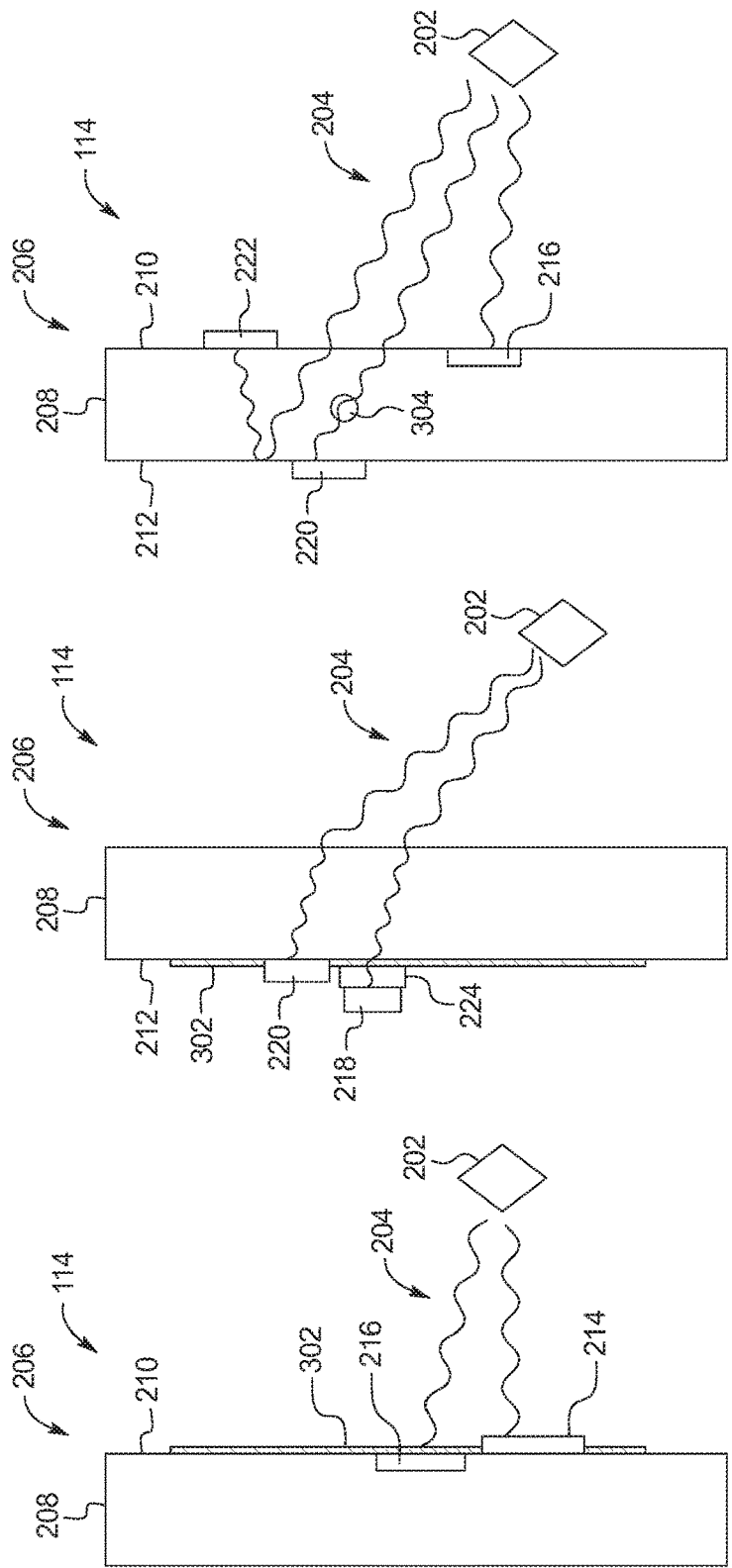
FIG. 3A depicts the opaqueness identification system detecting condensation on an interior surface of the window of FIG. 2.
FIG. 3B depicts the opaqueness identification system detecting condensation on an exterior surface of the window of FIG. 2.
FIG. 3C depicts the opaqueness identification system detecting an imperfection formed within the window of FIG. 2.

In some examples, the opaqueness detection assembly 114 of FIGS. 2-3C includes a grid of light sensors that extend across an area of the window 206 to enable the opaqueness controller 116 to detect a source of opaqueness within that area of the window 206. Further, in some examples, the grid of light sensors enables the opaqueness controller 116 to detect a location of the source of opaqueness within the area of the window 206 covered by the grid of light sensors. Additionally or alternatively, an opaqueness detection assembly 114 is located on the front windshield 102, the rear windshield 104, and/or one or more of the side windows 106 to enable the opaqueness controller 116 to identify whether a source of opaqueness is located on the front windshield 102, the rear windshield 104, and/or the one or more of the side windows 106, respectively.

Figure 4:
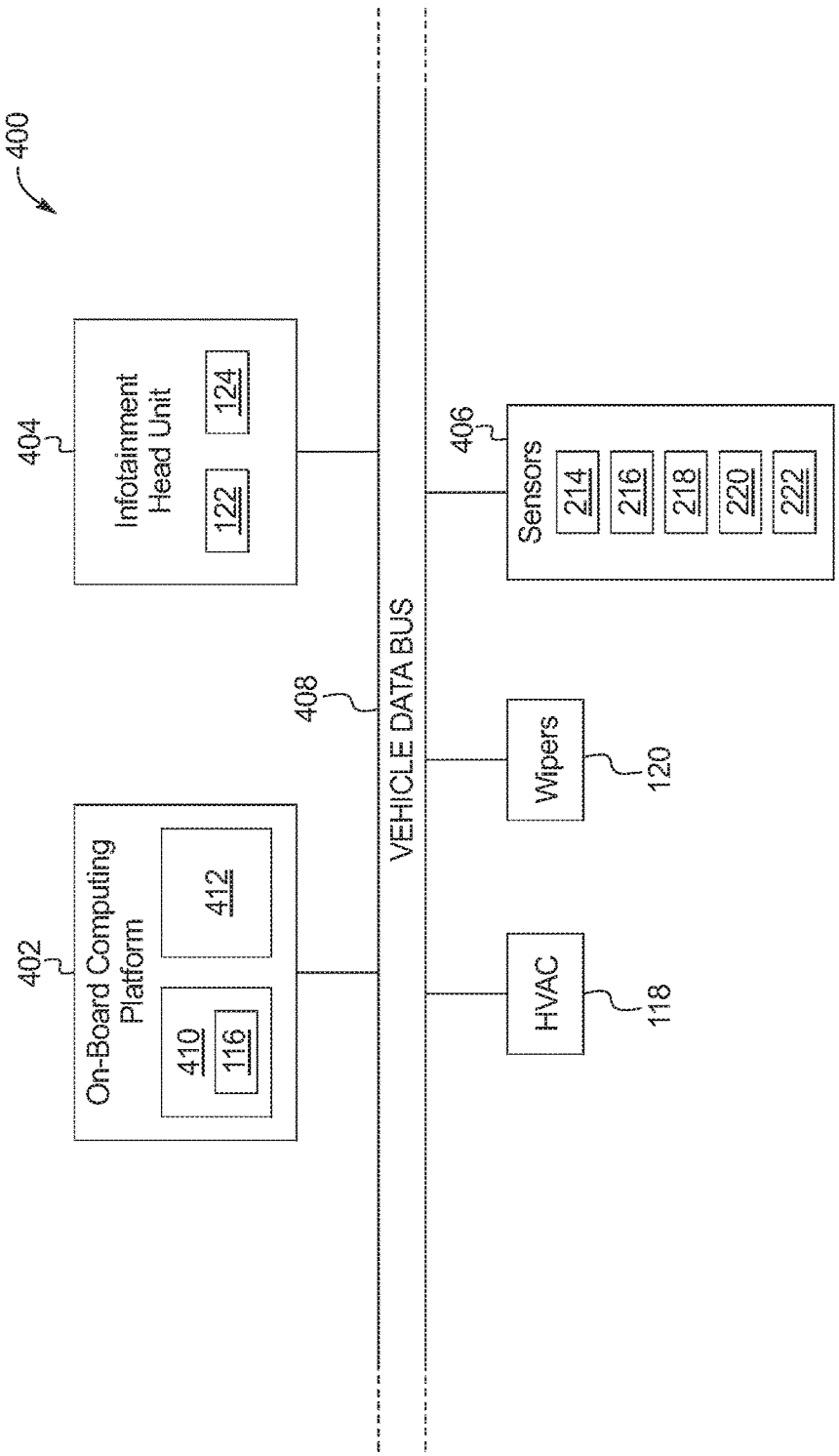
FIG. 4 is a block diagram of electronic components of the vehicle of FIG. 1.

FIG. 4 is a block diagram of electronic components 400 of the vehicle 100. As illustrated in FIG. 4, the electronic components 400 include an on-board computing platform 402, an infotainment head unit 404, the HVAC system 118, the windshield wipers 120, sensors 406, and a vehicle data bus 408.

The on-board computing platform 402 includes a microcontroller unit, controller or processor 410 and memory 412. In some examples, the processor 410 of the on-board computing platform 402 is structured to include the opaqueness controller 116. Alternatively, in some examples, the opaqueness controller 116 is incorporated into another electronic control unit (ECU) with its own processor 410 and memory 412. The processor 410 may be any suitable processing device or set of processing devices such as, but not limited to, a microprocessor, a microcontroller-based platform, an integrated circuit, one or more field programmable gate arrays (FPGAs), and/or one or more application-specific integrated circuits (ASICs). The memory 412 may be volatile memory (e.g., RAM including non-volatile RAM, magnetic RAM, ferroelectric RAM, etc.), non-volatile memory (e.g., disk memory, FLASH memory, EPROMs, EEPROMs, memristor-based non-volatile solid-state memory, etc.), unalterable memory (e.g., EPROMs), read-only memory, and/or high-capacity storage devices (e.g., hard drives, solid state drives, etc). In some examples, the memory 412 includes multiple kinds of memory, particularly volatile memory and non-volatile memory.

The memory 412 is computer readable media on which one or more sets of instructions, such as the software for operating the methods of the present disclosure, can be embedded. The instructions may embody one or more of the methods or logic as described herein. For example, the instructions reside completely, or at least partially, within any one or more of the memory 412, the computer readable medium, and/or within the processor 410 during execution of the instructions.

The infotainment head unit 404 provides an interface between the vehicle 100 and a user. The infotainment head unit 404 includes digital and/or analog interfaces (e.g., input devices and output devices) to receive input from and display information for the user(s). The input devices include, for example, a control knob, an instrument panel, a digital camera for image capture and/or visual command recognition, a touch screen, an audio input device (e.g., cabin microphone), buttons, or a touchpad. The output devices may include instrument cluster outputs (e.g., dials, lighting devices), actuators, the display 122 (e.g., a heads-up display, a center console display such as a liquid crystal display (LCD), an organic light emitting diode (OLED) display, a flat panel display, a solid state display, etc.), and/or the speakers 124. In the illustrated example, the infotainment head unit 404 includes hardware (e.g., a processor or controller, memory, storage, etc.) and software (e.g., an operating system, etc.) for an infotainment system (such as SYNC® and MyFord Touch® by Ford®, etc.). Additionally, the infotainment head unit 404 displays the infotainment system on, for example, the display 122.

The sensors 406 are arranged in and around the vehicle 100 to monitor properties of the vehicle 100 and/or an environment in which the vehicle 100 is located. One or more of the sensors 406 may be mounted to measure properties around an exterior of the vehicle 100. Additionally or alternatively, one or more of the sensors 406 may be mounted inside a cabin of the vehicle 100 or in a body of the vehicle 100 (e.g., an engine compartment, wheel wells, etc.) to measure properties in an interior of the vehicle 100. For example, the sensors 406 include accelerometers, odometers, tachometers, pitch and yaw sensors, wheel speed sensors, microphones, tire pressure sensors, biometric sensors and/or sensors of any other suitable type. In the illustrated example, the sensors 406 include the light sensor 214 (e.g., the first light sensor), the light sensor 216 (e.g., the second light sensor), the light sensor 218 (e.g., the third light sensor), the light sensor 220 (e.g., the fourth light sensor), and the light sensor 222 (e.g., the fifth light sensor).

The vehicle data bus 408 communicatively couples the HVAC system 118, the windshield wipers 120, the on-board computing platform 402, the infotainment head unit 404, and the sensors 406. In some examples, the vehicle data bus 408 includes one or more data buses. The vehicle data bus 408 may be implemented in accordance with a controller area network (CAN) bus protocol as defined by International Standards Organization (ISO) 11898-1, a Media Oriented Systems Transport (MOST) bus protocol, a CAN flexible data (CAN-FD) bus protocol (ISO 11898-7) and/a K-line bus protocol (ISO 9141 and ISO 14230-1), and/or an Ethernet™ bus protocol IEEE 802.3 (2002 onwards), etc.

Figure 5:
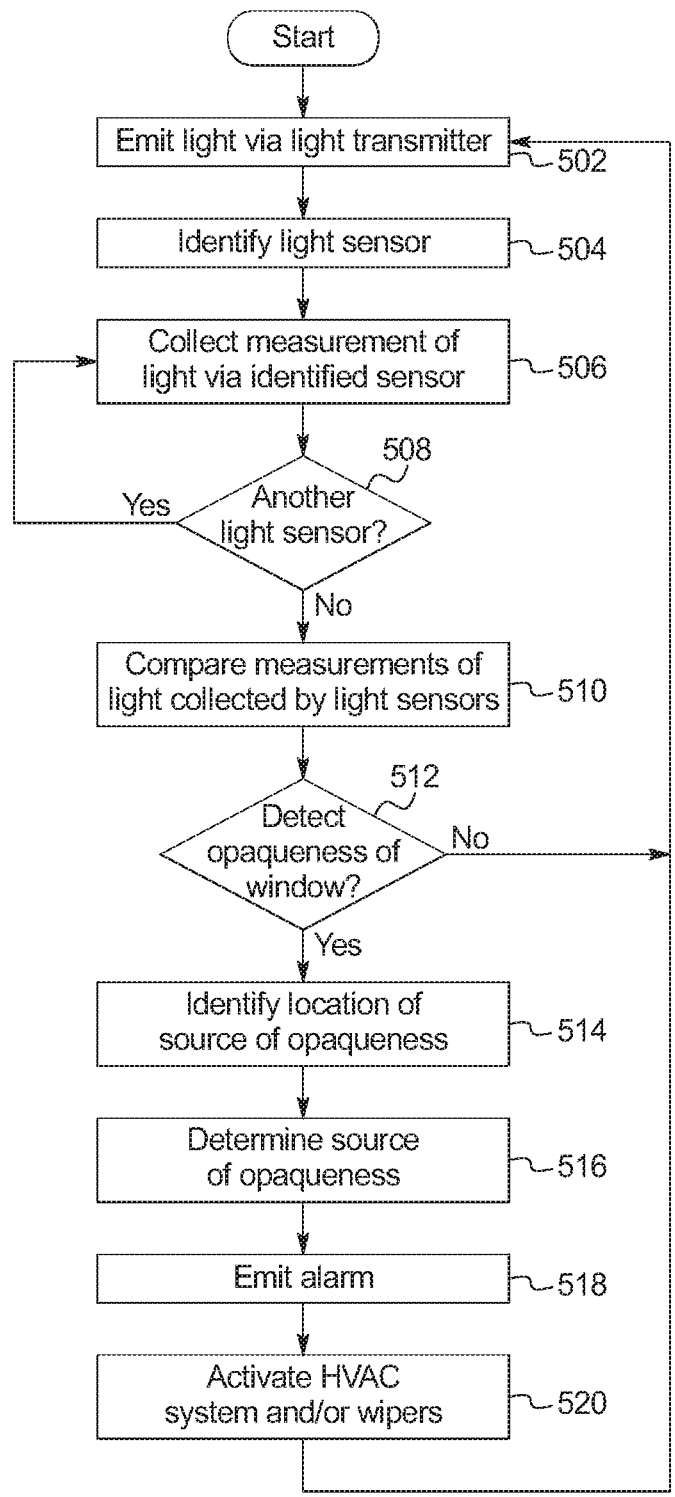
FIG. 5 is a flowchart for detecting and identifying opaqueness on and/or within a vehicle window in accordance with the teachings herein.

FIG. 5 is a flowchart of an example method 500 to detect and identify opaqueness on and/or within a vehicle window. The flowchart of FIG. 5 is representative of machine readable instructions that are stored in memory (such as the memory 412 of FIG. 4) and include one or more programs which, when executed by a processor (such as the processor 410 of FIG. 4), cause the vehicle 100 to implement the example opaqueness controller 116 of FIGS. 1 and 4. While the example program is described with reference to the flowchart illustrated in FIG. 5, many other methods of implementing the example opaqueness controller 116 may alternatively be used. For example, the order of execution of the blocks may be rearranged, changed, eliminated, and/or combined to perform the method 500. Further, because the method 500 is disclosed in connection with the components of FIGS. 1-4, some functions of those components will not be described in detail below.

Initially, at block 502, the light transmitter 202 emits the light 204. For example, the opaqueness controller 116 sends a signal to the light transmitter 202 to emit light (e.g., the light 204) having a predefined light intensity. At block 504, the opaqueness controller 116 identifies a light sensor of the opaqueness detection assembly 114 (e.g., the light sensor 214, the light sensor 216, the light sensor 218, the light sensor 220, or the light sensor 222 of FIGS. 2-4). At block 506, the opaqueness controller 116 collects a measurement of the light 204 (e.g., a measurement of the intensity of the light 204) that is collected by the identified light sensor. At block 508, the opaqueness controller 116 determines whether there is another light sensor (e.g., the light sensor 214, the light sensor 216, the light sensor 218, the light sensor 220, or the light sensor 222 of FIGS. 2-4) to identify. In response to the opaqueness controller 116 determining that there is another light sensor to identify, the method 500 returns to block 506. Otherwise, in response to the opaqueness controller 116 determining that there is no other light sensor to identify, the method 500 proceeds to block 510.

At block 510, the opaqueness controller 116 compares the measurements of the light 204 collected by the light sensors (e.g., the light sensor 214, the light sensor 216, the light sensor 218, the light sensor 220, or the light sensor 222). At block 512, the opaqueness controller 116 detects whether there is a source of opaqueness on and/or within the window 206 (e.g., the front windshield 102, the rear windshield 104, one of the side windows 106 of FIG. 1) on which the light sensors are located. For example, the opaqueness controller 116 detects whether there is a source of opaqueness based upon the comparison of the light measurements collected by the light sensors. In response to the opaqueness controller 116 detecting that there is not a source of opaqueness on and/or within the window 206, the method 500 returns to block 502. Otherwise, in response to the opaqueness controller 116 detecting that there is a source of opaqueness on and/or within the window 206, the method 500 proceeds to block 514.

At block 514, the opaqueness controller 116 identifies a location of the source of opaqueness relative to the window 206. For example, the opaqueness controller 116 identifies that the source of opaqueness is on the interior surface 210 of the window 206 in response to the opaqueness controller 116 determining that a first measurement of the light 204 collected by the light sensor 214 is greater than a second measurement of the light 204 collected by the light sensor 216 by at least a first predetermined value. The opaqueness controller 116 identifies that the source of opaqueness is on the exterior surface 212 of the window 206 in response to the opaqueness controller 116 determining that a third measurement of the light 204 collected by the light sensor 216 is less than a fourth measurement of the light 204 collected by the light sensor 220 by at least a second predetermined value. The opaqueness controller 116 identifies that the source of opaqueness is within the layer 208 of the window 206 in response to the opaqueness controller 116 determining that the fourth measurement of the light 204 collected by the light sensor 220 is less than the second measurement of the light 204 collected by the light sensor 216 by at least a third predetermined value. Additionally or alternatively, the opaqueness controller 116 identifies that the source of opaqueness is within the layer 208 of the window 206 in response to the opaqueness controller 116 determining that the fourth measurement of the light 204 collected by the light sensor 220 is less than a fifth measurement of the light 204 collected by the light sensor 222 by at least a fourth predetermined value.

At block 516, the opaqueness controller 116 determines the source of opaqueness based upon the comparison of the light measurements collected by the light sensors. For example, the opaqueness controller 116 determines that the source of opaqueness is frost on the interior surface 210 based upon the difference in light measurements of the light sensors 214, 216. The opaqueness controller 116 determines that the source of opaqueness is rain, ice, snow, and/or dirt on the exterior surface 212 based upon the difference in light measurements of the light sensors 218, 220. The opaqueness controller 116 determines that the source of opaqueness is an imperfection (e.g., the imperfection 304) is within the layer 208 of the window 206 based upon the difference in light measurements of the light sensors 216, 220 and/or the light sensors 220, 222. At block 518, the opaqueness controller 116 emits an alarm (e.g., via the display 122 and/or the speakers of FIGS. 1 and 4) indicating that a source of opaqueness has been detected on the window 206. At block 520, the opaqueness controller 116 activates and/or adjusts the HVAC system 118 and/or the windshield wipers 120 based upon the detected source of opaqueness. For example, the opaqueness controller 116 activates and/or adjusts the HVAC system 118 in response to determining that the source of opaqueness is condensation along the interior surface 210 of the window 206. Additionally or alternatively, the opaqueness controller 116 activates and/or adjusts the windshield wipers 120 in response to determining that the source of opaqueness is located along the exterior surface 212 of the window 206.

In this application, the use of the disjunctive is intended to include the conjunctive. The use of definite or indefinite articles is not intended to indicate cardinality. In particular, a reference to "the" object or "a" and "an" object is intended to denote also one of a possible plurality of such objects. Further, the conjunction "or" may be used to convey features that are simultaneously present instead of mutually exclusive alternatives. In other words, the conjunction "or" should be understood to include "and/or". The terms "includes," "including," and "include" are inclusive and have the same scope as "comprises," "comprising," and "comprise" respectively.

The above-described embodiments, and particularly any "preferred" embodiments, are possible examples of implementations and merely set forth for a clear understanding of the principles of the invention. Many variations and modifications may be made to the above-described embodiment(s) without substantially departing from the spirit and principles of the techniques described herein. All modifications are intended to be included herein within the scope of this disclosure and protected by the following claims.

What is claimed is:

1. A vehicle comprising:
   a window including an interior surface and an exterior surface;
   a light transmitter to emit light;
   light sensors to measure the light and including:
      a first sensor offset from and a second sensor aligned with the interior surface; and
      a third sensor offset from and a fourth sensor aligned with the exterior surface; and
   a controller for detecting a source of opaqueness of the window via the light sensors.

2. The vehicle of claim 1, wherein the window is a windshield.

3. The vehicle of claim 1, wherein the second sensor is embedded within the window.

4. The vehicle of claim 1, further including a bracket coupled to the exterior surface via adhesive, the third sensor being offset from the exterior surface via the bracket.

5. The vehicle of claim 1, wherein the controller detects that the source of opaqueness includes condensation on the interior surface responsive to determining a first measurement of the first sensor is greater than a second measurement of the second sensor by at least a first predetermined value.

6. The vehicle of claim 5, wherein the controller identifies that frost is on the window responsive to detecting that the source of opaqueness includes the condensation on the interior surface.

7. The vehicle of claim 5, further including an HVAC system that the controller activates responsive to the controller detecting that the source of opaqueness includes the condensation on the interior surface of the window.

8. The vehicle of claim 1, wherein the controller detects that the source of opaqueness includes condensation on the exterior surface responsive to determining a third measurement of the third sensor is less than a fourth measurement of the fourth sensor by at least a second predetermined value.

9. The vehicle of claim 8, wherein the controller identifies that rain, snow, ice, or dirt is on the window based upon a difference between the third measurement and the fourth measurement.

10. The vehicle of claim 8, further including wipers that the controller activates responsive to the controller detecting the source of opaqueness on the exterior surface of the window.

11. The vehicle of claim 1, wherein the controller detects that the source of opaqueness is within the window responsive to determining a fourth measurement of the fourth sensor is less than a second measurement of the second sensor by at least a third predetermined value.

12. The vehicle of claim 1, wherein:
   the light sensors include a fifth sensor coupled to the interior surface, the fifth sensor facing away from the light transmitter in a direction opposite to the first sensor; and
   the controller detects that the source of opaqueness is within the window responsive to determining a fourth measurement of the fourth sensor is less than a fifth measurement of the fifth sensor by at least a fourth predetermined value.

13. The vehicle of claim 1, wherein the controller identifies that there is an imperfection within the window responsive to detecting that that the source of opaqueness is within the window.

14. The vehicle of claim 13, wherein the controller sends a signal to emit an alert responsive to the controller detecting that the source of opaqueness is within the window.

15. A method comprising:
   emitting light via a light transmitter;
   collecting measurements of the light via light sensors including:
      a first sensor offset from and a second sensor aligned with an interior surface of a vehicle window; and
      a third sensor offset from and a fourth sensor aligned with an exterior surface of the vehicle window; and detecting, via a processor, a source of opaqueness of the vehicle window based upon a comparison of the measurements.

16. The method of claim 15, wherein collecting the measurements via the light sensors includes collecting a first measurement via the first sensor, a second measurement via the second sensor, a third measurement via the third sensor, and a fourth measurement via the fourth sensor.

17. The method of claim 16, wherein detecting the source of opaqueness includes:
   detecting that the source of opaqueness includes condensation on the interior surface responsive to determining the first measurement is greater than the second measurement by at least a first predetermined value; and
   detecting that the source of opaqueness includes condensation on the exterior surface responsive to determining the third measurement is less than the fourth measurement by at least a second predetermined value.

18. The method of claim 17, further including activating an HVAC system responsive to detecting that the source of opaqueness includes the condensation on the interior surface.

19. The method of claim 17, further including activating wipers responsive to detecting that the source of opaqueness includes the condensation on the exterior surface.

20. The method of claim 16, wherein detecting the source of opaqueness includes detecting that the source of opaqueness is within the vehicle window responsive to determining the fourth measurement is less than the second measurement by at least a third predetermined value.

* * * * *